US008361416B2

(12) United States Patent
Berner et al.

(10) Patent No.: US 8,361,416 B2
(45) Date of Patent: Jan. 29, 2013

(54) CONTAINER FOR THE PREPARATION, PRESERVATION AND STORAGE OF BIOLOGICAL SAMPLES USING A DRYING AGENT

(75) Inventors: Alexander Berner, Dachau (DE); Bernhard Hostettler, Gockhausen (CH)

(73) Assignee: Prionics AG, Schlieren (CH)

( * ) Notice: Subject to any disclaimer, the term of this patent is extended or adjusted under 35 U.S.C. 154(b) by 286 days.

(21) Appl. No.: 12/812,216

(22) PCT Filed: Jan. 22, 2009

(86) PCT No.: PCT/EP2009/000379
§ 371 (c)(1), (2), (4) Date: Jul. 8, 2010

(87) PCT Pub. No.: WO2009/095178
PCT Pub. Date: Aug. 6, 2009

(65) Prior Publication Data

US 2010/0291662 A1 Nov. 18, 2010

(30) Foreign Application Priority Data

Jan. 28, 2008 (DE) ......................... 10 2008 007 352

(51) Int. Cl.
*A61B 10/00* (2006.01)

(52) U.S. Cl. .......... 422/536; 422/63; 422/544; 422/547; 422/560; 422/561

(58) Field of Classification Search ................ 422/9, 50, 422/500–502, 63–67, 536, 544, 547, 560–561
See application file for complete search history.

(56) References Cited

U.S. PATENT DOCUMENTS 3,388,043 A * 6/1968 Ingvorsen ................. 435/309.1
4,073,693 A 2/1978 Janin
4,834,234 A 5/1989 Sacherer et al.
4,865,813 A 9/1989 Leon
4,954,149 A 9/1990 Fullemann
5,573,951 A * 11/1996 Gombrich et al. ......... 435/289.1
6,426,049 B1 7/2002 Rosen et al.
2007/0202538 A1 8/2007 Glezer et al.
2007/0297939 A1 12/2007 Chiocca et al.

FOREIGN PATENT DOCUMENTS

DE 507359 9/1930
DE 19957861 A1 6/2001
DE 10028482 A1 12/2001

(Continued)

*Primary Examiner* — Jyoti Nagpaul
(74) *Attorney, Agent, or Firm* — Rankin, Hill & Clark LLP

(57) ABSTRACT

The invention relates to a sample container (10, 100, 500, 700) for biological sample material (23, 230), comprising an upper opening (11) that can be closed by a lid (14, 140, 540), a lateral wall region (12) and a base (13) and a hygroscopic substance (19, 190, 590, 790) contained in the interior of the sample container for drying sample material (23, 230) in the sample container, wherein the sample container is partitioned into at least two compartments, of which one is a sample compartment (16, 160, 560), and the other is a drying compartment (18, 180, 580) containing the hygroscopic substance, wherein the hygroscopic substance is connected to the interior of the sample container in a steam exchange connection, and wherein the sample compartment extends from an upper end, particularly equipped with an opening (40, 400), in the longitudinal direction to the opening in a flush manner to the base (13) of the sample container.

14 Claims, 6 Drawing Sheets

FOREIGN PATENT DOCUMENTS

Figure 1:
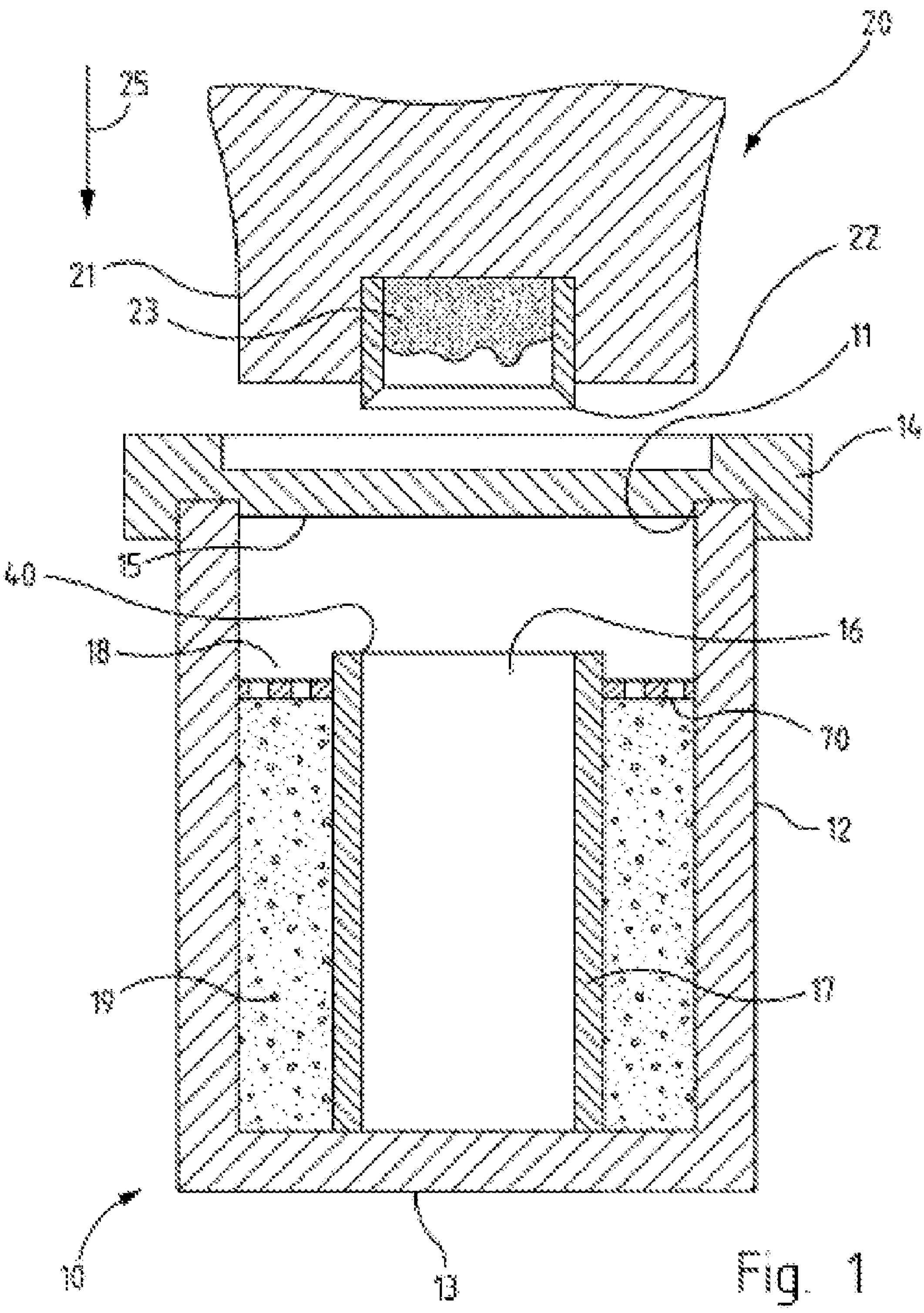

| | | | |
|---|---|---|---|
| EP | 0290920 | A2 | 11/1988 |
| EP | 1162463 | A2 | 12/2001 |
| WO | 92/20449 | A1 | 11/1992 |
| WO | 01/28683 | A1 | 4/2001 |
| WO | 01/40762 | A1 | 6/2001 |
| WO | 2009/095178 | A1 | 8/2009 |

* cited by examiner

CONTAINER FOR THE PREPARATION, PRESERVATION AND STORAGE OF BIOLOGICAL SAMPLES USING A DRYING AGENT

The invention concerns a sample container for biological sample material as well as a device, for the preparation, preservation and storage of sample material, in the context of which such a sample container is utilized.

Normally biological material is not processed directly after its preparation. In some cases the sample material is to be stored subsequent to its preparation only for an eventual processing at a later date. In other cases a subsequent processing ensues routinely, wherein the time interval between preparation and processing depends on a sequence of logistic and other factors.

It is to be noted that for example in biological tissue samples decomposition processes start immediately after the preparation whose degree is dependent, among other things, on the moisture content of the sample. If for example in the context of sequential examinations of animals a plurality of samples are initially collected and only sent to the laboratory after a certain time span, the storage of the prepared sample materials can, without preservation in the form of drying, cooling etc, have the effect that a significant percentage of the prepared sample material is no longer useable for further processing.

In this context a sample container has become known from DE 199 57 861 in which a hygroscopic substance is contained as a drying agent. This known sample container makes a direct preservation of the sample material at the preparation site possible, in the context of which in particular the protein and nucleic acid components can be stabilized.

One problem with this type of sample container is that the sample material that has been placed in the sample container can be mixed with the drying agent, for example in the context of an automated withdrawal of the sample material from the sample container, which can present interference particularly during the subsequent processing.

It is therefore the object of the invention, starting from prior art, to create a sample container that avoids the mentioned disadvantages and that can be integrated in a particular simple manner into a device utilized for example in connection with an ear mark for the preparation of sample material.

The problem is solved with a sample container that features the characteristic features of claim 1 as well as a device for the preparation and storage of sample material according to claim 8.

As is known from prior art, the sample container according to the invention also features an upper opening which can be closed by means of a lid, as well as a lateral wall region and a base. The interior of the sample container contains a hygroscopic substance for the drying of the sample material. Furthermore the sample container is divided into at least two compartments of which one (sample compartment) can receive for example the sample and the other is a drying compartment that features the hygroscopic substance. The hygroscopic substance is thereby in a steam exchange connection with the interior of the sample container and, as the case may be, the sample compartment.

By steam exchange connection it is meant that the moisture that is leaving the sample is absorbed by the hygroscopic substance. The characteristics and amount of the hygroscopic substance are thereby adapted to the desired drying effect or the sample material to be dried. The selection of suitable substances and their dosing does not represent a problem for the person skilled in the art and shall not be further explained here.

According to the invention it is provided that the sample compartment features an upper opening, in its upper end, which is oriented toward the opening of the sample container. The sample compartment extends from its upper end in the longitudinal direction to the opening in a flush manner downward to the base of the sample container, wherein, as is described further below, the base of the sample container can feature an opening in the area of the sample compartment. The opening in the upper end of the sample compartment can then be closed by means of for example a penetrable lid or wall area.

The terms sample compartment and drying compartment are to be interpreted broadly.

The sample compartment can for example encompass an area in which the sample material is received for storage. The term also covers an area that simply serves to guide the sample material during its removal from the sample container for purposes of further processing. Finally the sample compartment can also already contain reagents that permit the processing of the sample material. These different possibilities are discussed in detail further below.

The term drying compartment is also to be interpreted broadly. This can entail an area in the interior of the sample container, which is for example partitioned off by a wall, in which the hygroscopic substance is disposed. Covered by the term drying compartment are however also form parts with hygroscopic characteristics that are disposed or implemented within the interior of the sample container.

It can obviously also be contemplated that particularly the drying compartment is separated into still additional compartments. One could for example envision that compartments with different hygroscopic substances or characteristics are provided that conceivably are more suitably adapted to certain drying conditions.

In contrast to prior art thereby an area is provided, according to the invention, that runs in a longitudinal direction through the sample container, meaning from its opening to its base that is facing the opening, said area being free of hygroscopic substance. This is particularly of an advantage during the automated removal of the sample by means of a stamp that was inserted from above through the sample container, as is described further below (for example see FIG. 3). In particular during such a removal the sample material can be removed for the purpose of processing from the sample container without, for the most part, spreading of hydroscopic substance that is possibly contained in the sample container In this context it is not necessarily required, as is explained still further below, that the sample material is received after its preparation in the sample compartment. Depending on the techniques employed it is also possible that the sample material remains initially still in the area of the opening of the sample container above the sample compartment and is only later, during the removal of the sample by means of the stamp, pressed out of this area out of the sample container, being guided through the sample compartment in a downward direction. This is however just one possibility. It is of course also conceivable that the sample is prepared by another means and is inserted by means of a tweezers or another suitable instrument directly into the sample compartment.

It is understood that the upper end of a sample compartment, which is partitioned by means of a wall, is positioned in the sample container in such a way that a steam exchange connection between for example the hygroscopic substance that is contained in the drying compartment and the sample can be implemented independently of whether the sample material is fixated above the sample compartment or disposed in the compartment. In a variation of the drying compartment in the shape of a hygroscopic form part there exists, in contrast, a direct steam exchange connection to the interior of the sample compartment. In the case of this variation the upper end of the sample compartment can therefore be disposed as desired.

Preferred embodiments of the invention are addressed in the sub claims.

In a preferred embodiment it is provided that the drying compartment is a form part that contains the hygroscopic substance. It is for example conceivable that the hygroscopic substance is embedded in a plastic of which then for example a foil material can be manufactured that, subsequent to insertion or placement in the sample container, represents the drying compartment there. In prior art such plastic materials are known, for example manufacturable using injection molding, that can feature up to 70% of hygroscopic substance (for example molecular sieve). Conceivable is of course also to generate drying installations by means of injection molding with other suitable forms from such plastic materials and to then insert these. Of course it is also possible in the context of the invention to already implement the drying compartment, by means of an adapted injection molding process, during the manufacture of sample container within the same.

Besides the discussed injection molding process other processes are of course also possible, such as for example extrusion and rolling.

In a further advantageous embodiment it can be provided that a form part that is implementing a drying compartment is manufactured by means of pressing, sintering or extrusion of hydroscopic substance. In the context of this embodiment it is also possible to give the drying compartment the desired shape. In the case of this embodiment it in all likelihood concerns a form part that is manufactured separately and is then inserted as a drying compartment into a sample container.

In a further embodiment of the invention it is provided that the sample compartment is delimited against a drying compartment, in which hygroscopic substance is placed, by at least one wall that is implemented in the sample container.

The wall that is delimiting the sample compartment as well as the wall area and base of the sample container can be manufactured from all materials known in this context. Suitable are particularly plastics but also glass.

The following additional embodiments of the sample container can be realized in connection with each of the embodiments of the drying compartment discussed above.

In order to assure a mostly even drying of the sample one can provide, according to a preferred embodiment, that the sample compartment is surrounded by the drying compartment.

Constructively this can be realized in the particularly simplest manner using usually round sample containers if, as provided in a further preferred embodiment, the sample compartment is a hollow cylinder, implemented with spacing relative to the side wall of the sample container, whose lower end is closed by means of the base of the sample container.

According to a further preferred embodiment the sample container according to the invention features a sample compartment whose opening that is provided in the area of its upper end is closed by means of a penetrable wall section and in which an opening is provided in an area of the base that is covered by the cross section of the drying compartment. Such a sample container can be manufactured particularly easily, for example by means of an injection molding process. At the same time it is assured that no hygroscopic substance whatsoever can enter the sample compartment.

According to a further preferred embodiment the sample container according to the invention features a sample compartment within which a separate area is implemented by means of a penetrable transverse wall. In the separate area suitable reagents, particularly in liquid form, can be placed for the treatment of the sample material.

According to the invention it is provided that the sample container is closed by means of a lid. The lid prevents the exit of the hydroscopic substance as well as an entry of moisture. Furthermore contaminations of the interior space of the sample container can be thereby avoided.

During conventional sample-taking it is provided that the lid can be removed in the course of the sample-taking and be replaced again after the arrangement of the sample materials in sample container.

It is however also conceivable that the lid is implemented such that it can be penetrated, as provided in a preferred embodiment. To this end a weakened section can for example be provided in the lid. This embodiment makes particularly sense in the context of utilizing a sample preparation agent, such as is for example known from EP 1 088 212. This sample preparation agent features a stamping device on its lower end and is dimensioned in such a way that it can, subsequent to the penetration of the lid of a sample container, close the sample container on its own. This is still further discussed below in connection with the device for sample preparation that is also covered by the invention.

Of course the described sample preparation agent can also be utilized with a sample container whose lid is not penetrable. In this case the lid must be removed manually and then the sample preparation agent is inserted into the container as described above. Even in this case it can be provided that the lower end of the sample preparation agent closes the container in that case instead of the originally provided lid.

Furthermore it can be provided that the base area of the sample container features a weakened area in the cross section that is covered by sample compartment. This weakened section could facilitate a pressing-out of the sample through the base of the sample container by means of the stamp mentioned above.

The hygroscopic substance that is provided in the drying compartment according to the invention can preferably be zeolite, silica gel or molecular sieve. Preferably the fine-grained or powdered form of such substances is utilized.

As just discussed, the invention concerns also a device for the preparation and storage of sample material, with

- a sample container according to the invention that features in particular a penetrable lid and
- a sample preparation agent that can be guided with its lower end through the penetrable lid of the sample container into the same, wherein the lower end is then disposed in the sample container in a defined position above and with a spacing to the upper opening of the sample compartment, and wherein at the lower end of the sample preparation agent is provided a cutting or stamping device by means of which a sample can be obtained particularly during the guiding of the lower end through tissue and wherein
- the position of the cutting or stamping device on the lower end of the sample preparation agent and the upper end of the sample compartment in the sample container are adapted to one another in such a manner that a sample obtained with the cutting or stamping device is located above the sample compartment, subsequent to insertion of the sample preparation agent into the sample container, or falls into the same.

The described sample preparation agent can be used by itself for the purpose of sample preparation and, in the process, be moved for example manually or automatically.

It is also conceivable that the sample preparation agent and the sample container are components of an ear mark that is utilized for the simultaneous marking and sample-taking from animals.

Such an ear mark is described in EP 1 088 212 in detail. In the context of the ear mark that is described there the sample preparation agent is located at the open end of a spike that is disposed at the male part of the ear mark. The ear mark furthermore contains a female part at which the sample container is disposed. During the process of marking/sample-taking with a suitable device, for example a pair of pliers, the female and male part of the ear mark are each disposed on different sides of the animal ear. Then the mandrel is pressed with the pair of pliers, with the sample preparation agent leading, through the ear, whereby a sample is stamped out. After passage of the ear the sample preparation agent, which is pushed by the mandrel, enters the sample container that is provided at the female part of the ear mark and closes it while at the same time a bordering area of the mandrel is interlocked with the female part of the ear mark. Mandrel and sample preparation agent are releasably connected with one another so that the sample container that is now closed with the preparation agent can be removed from the female part while the mark remains in the ear.

As was previously stated, this is a variation that can be utilized in particular for the marking and sample-taking from animals in the area of the ear. The invention is of course not limited to such adapted systems. It is also conceivable that the system encompasses only the sample preparation agent and the sample container. Of significance in the context of this system is that the sample preparation agent after the penetration of the lid is positioned in such a manner that its cutting or punching device is located centrally above the opening of the sample compartment. As a result the sample is either held above the sample compartment or can fall from the same into the compartment, for example during the course of the progressing drying. It is also conceivable that, as in a preferred embodiment, the lower end of the sample preparation agent closes the sample container. It is however also conceivable that a separate lid is provided by means of which the sample container is closed after a sample preparation agent was utilized that is not capable of closing the container.

A further preferred embodiment provides, as was mentioned above already, that the device is a component of an earmark for the marking of animals.

In what follows the invention shall be further explained based on illustrations that represent several embodiments.

Figure 2:
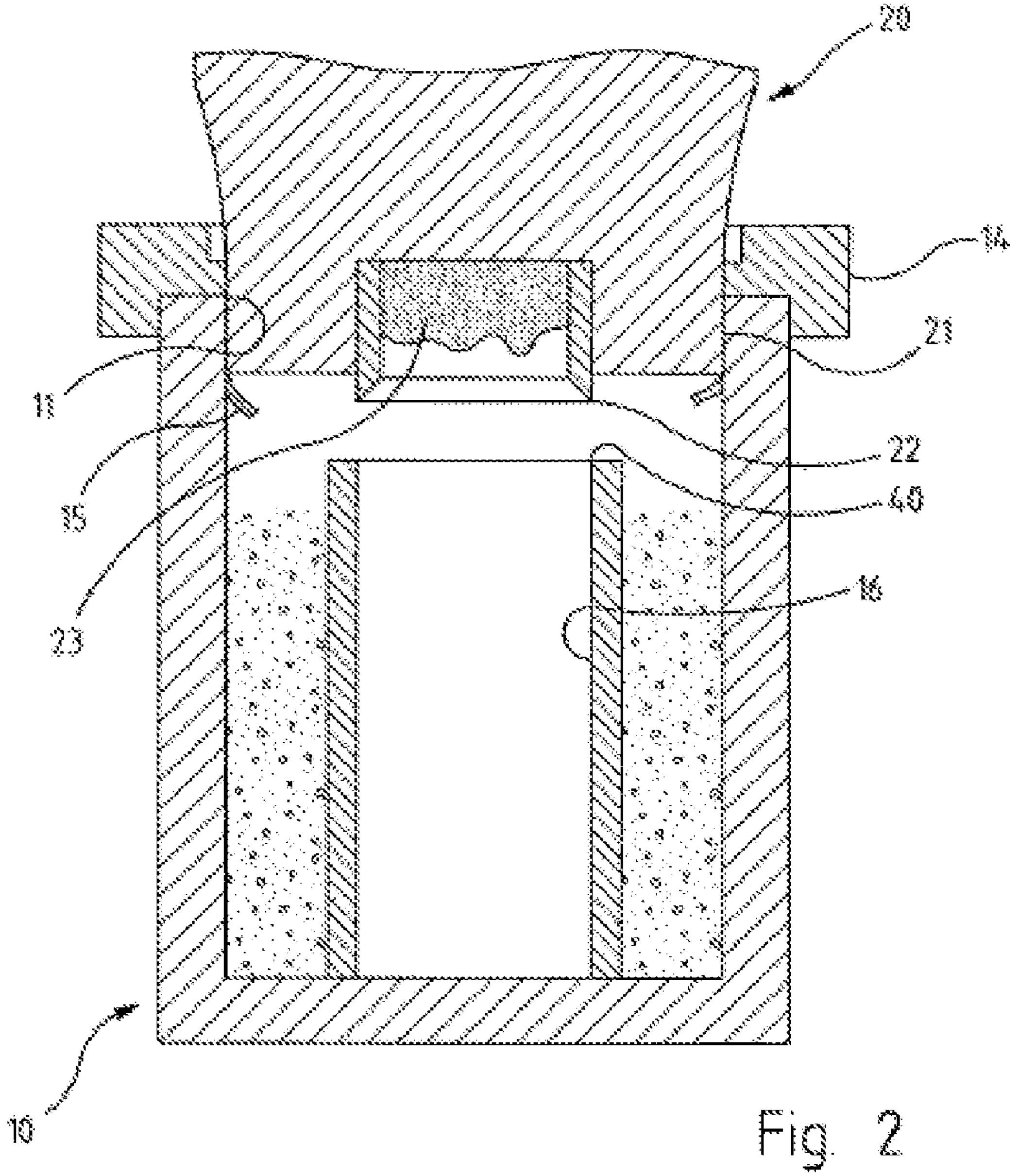
Figure 3:
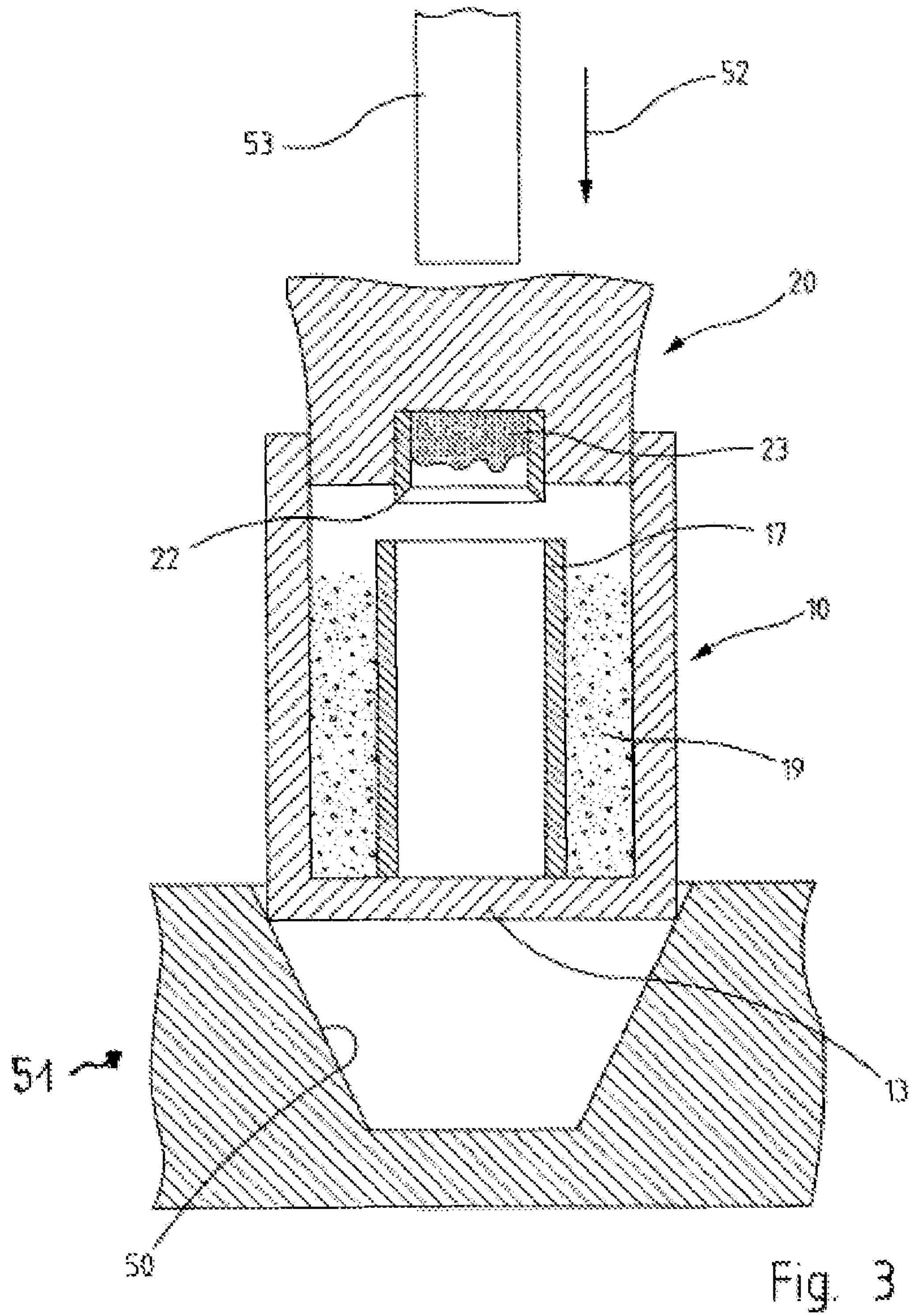
Figure 4:
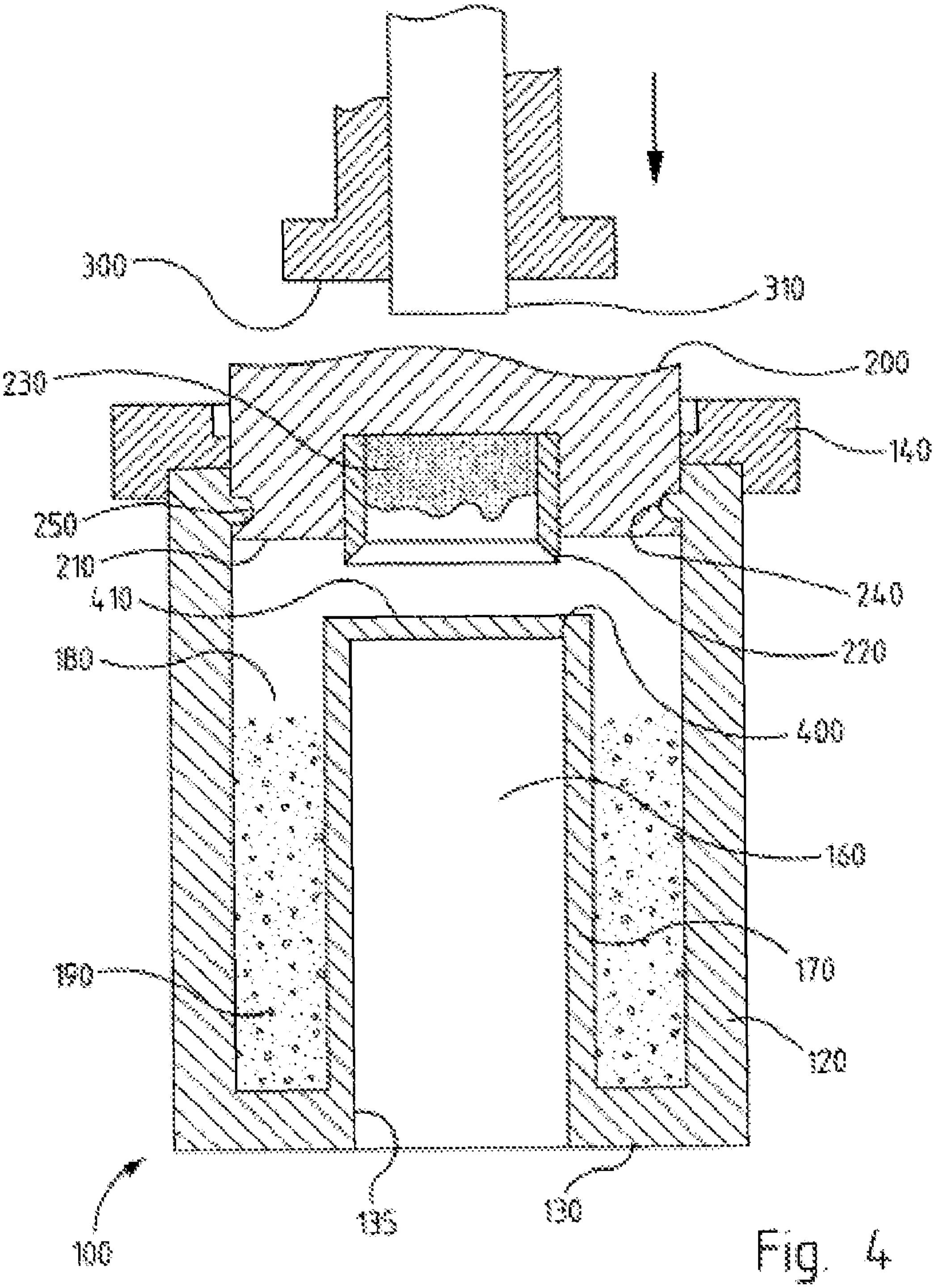
Figure 5:
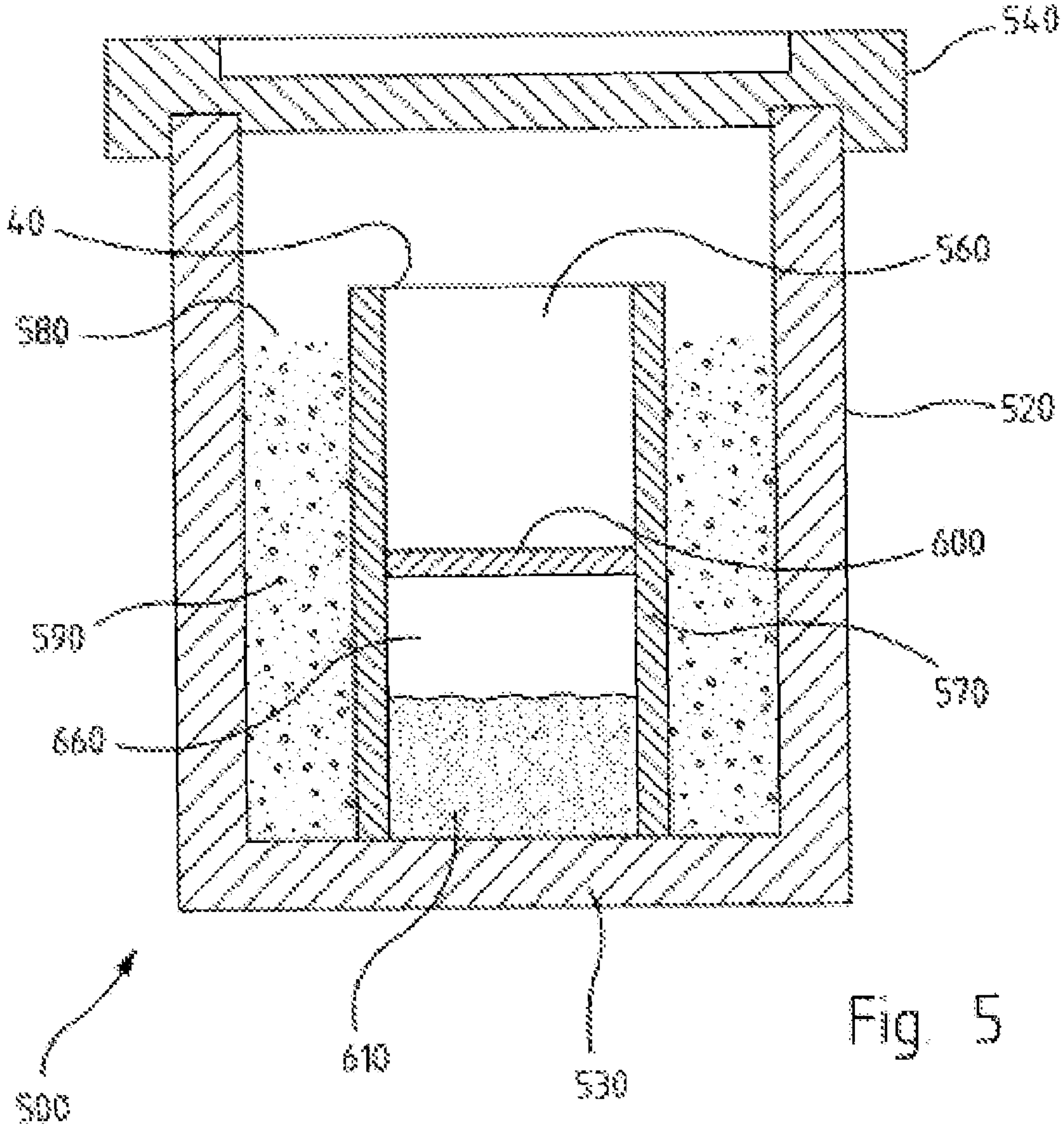
Figure 6:
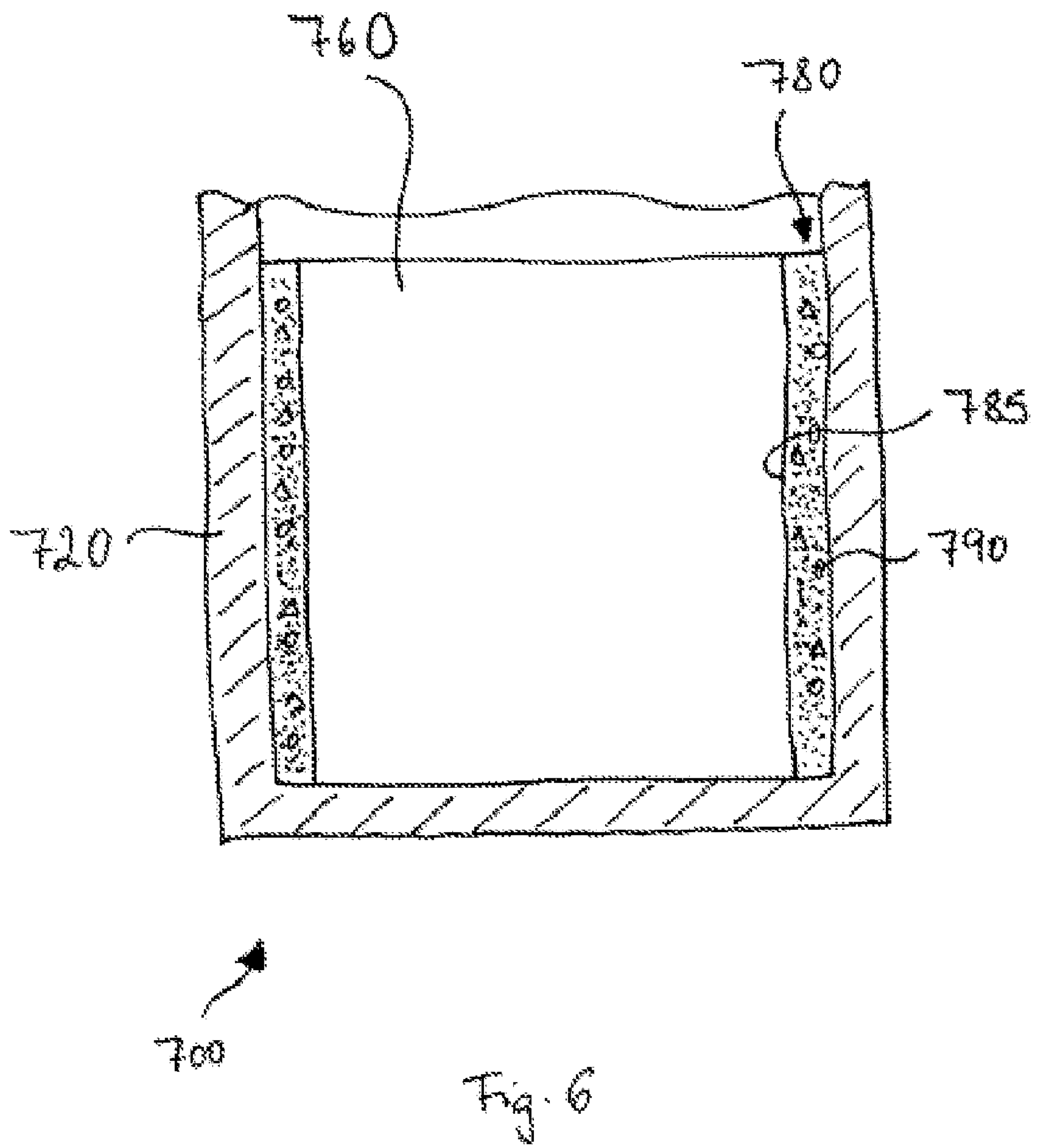

The drawings show:

FIG. 1 a sample container prior to the insertion of the probe,

FIG. 2 the container from FIG. 1 after the insertion of the probe,

FIG. 3 the sample container from FIG. 2 prior to the removal of sample material for purposes of its processing, FIGS. 4-6 additional embodiments of the sample container.

FIG. 1 presents a sample container 10 with an upper opening 11, a lateral wall region 11, a lateral wall region 12, as well as a base 13. The sample container 10 is closed with a lid 14 which is implemented in its central region 15 in such a way that it can be penetrated. In the sample container 10 a sample compartment 16 is implemented in the shape of a hollow cylinder with an upper opening 40. The sample compartment 16 extends flush with this opening 40 in a longitudinal direction downward to the base 13. The sample compartment is delimited by a circumferentially running wall 17.

Furthermore a drying compartment 18, which encompasses the sample compartment 16, is implemented in the sample container 10. The drying compartment 18 is open in the upward direction and is delimited laterally by the lateral wall region 12 as well as the wall 17 and in the downward direction by the base 13 of the sample container 10. In the drying compartment 18 a hygroscopic substance 19 is provided which, as can be discerned from FIG. 1, is in a steam exchange connection with the interior of the sample container 10 as well as the interior of the sample compartment 16.

In order to avoid that the hygroscopic substance 19 distributes itself in the sample container 10, the substance can for example be pressed into the compartment 18. It is also conceivable to for example cover the upper layer with a sieve 70, which is only represented in FIG. 1, or other such device, for example a semi-permeable membrane that holds the substance in place. Of course it also possible to fixate the hydroscopic substance 19 by means of adhesion etc. Critical however is that through such measures the steam exchange rate is not diminished to the degree that the desired drying of the sample material in the sample container 10 no longer occurs or no longer occurs effectively.

Furthermore FIG. 1 presents a sample preparation agent 20, which is schematically indicated above the sample container 10, with a lower end 21 in which a stamping device 22 is disposed.

In the demonstrated case biological sample material 23 was already prepared with the sample preparation agent 20, said material was pressed into the stamping device 22 and remains there for the time being. During the subsequent course of the sample preparation and processing the sample preparation agent 20 is moved in the direction of the arrow 25. The circumstance that then arises is represented in FIG. 2.

In FIG. 2 the sample preparation agent 20 has now penetrated, with its lower end 21, the lid 14 of the sample container 10 in its centrally located weakened area 15 and closes now itself the upper opening 11. One recognizes that the stamping device 22 and the sample compartment 16 are aligned relative to one another in such a manner that the sample material 23 is located directly above the opening 40.

In FIG. 3 the sample container, in the state shown in FIG. 2, is inserted into a vessel 50 of an otherwise only schematically represented microtiter plate 51. A stamp 53 moves from above in the direction of an arrow 52 toward the sample container 10 and the sample preparation agent 20 that is disposed thereon. During the subsequent course of its movement the lower end of the stamp 53 will penetrate the sample preparation agent 20, pressing the biological sample material 23 from the cutting and stamping device 22 into the sample compartment 17, through the same and the base 13 of the sample container 10, into the vessel 50.

From FIG. 3 it follows that the sample material 23 that is moved by means of the stamp 53 through the sample container 10 does not come in contact with the hygroscopic substance 19. In order to assure that after the penetration of the base 13 also no hygroscopic substance exits alongside, a ring-shaped bracing or such-like type of installation can be provided for example in the base area of the drying compartment, said installation prevents an exit of hygroscopic substance also in the case where the base 13 is destroyed in the area of the drying compartment 18.

The purpose of the sample compartment that is provided in the sample container according to the invention can, as was referred to above already, for example be in the reception of biological sample material but also in its guidance during the removal from the container and/or the processing.

The FIGS. 4 and 5 concern embodiment examples of the sample container according to the invention in which (FIG. 4) the guidance of the sample material or (FIG. 5) its processing are of primary importance.

The embodiment example of a sample container 100 according to the invention, which is shown in FIG. 4, again features a lid 140, lateral wall regions 120 as well as a base 130. In the sample container 100 a sample compartment 160 is provided which is delimited by a wall 170. A drying compartment 180 is provided, which contains the hygroscopic substance, that surrounds the sample compartment 160. The drying compartment 180 is delimited by the wall 170 or the lateral wall area 120.

The sample compartment 160 features an upper opening 400 which, in contrast to the embodiment example shown so far in the FIGS. 1-3, is closed by means of a lid or a wall region 410.

In this embodiment example also the sample compartment that is flush with the upper opening 400 reaches in a downward direction to the base 130 of the sample container 100, whereby however in this case the base region 130 in the part of the cross section that is covered by the sample compartment 160 is not implemented, or therefore open.

A particular advantage of this embodiment example is that, as is explained below, no hygroscopic substance 190 can reach into the sample compartment.

The sample preparation can occur in this embodiment example also by means of a sample preparation agent 200 that features a lower end 210 in which a cutting and stamping device 220 is provided. In the case shown the biological sample material 230 was already prepared with the cutting and stamping device 220, said material was pressed, as was the case in the other shown embodiment examples, in the course of the preparation into the stamping device 220 and remains there for the time being.

One furthermore recognizes that a circumferentially running protrusion 240 is implemented in the lateral wall region 120 of the sample container, into said protrusion the sample preparation agent 200 was locked with a correspondingly circumferentially running groove 250. The sample preparation agent 200 remains in this position during a time period between preparation and processing.

The connection between groove 250 and protrusion 240 is chosen such that by means of further pressing, for example with an only schematically indicated ring-shaped broad stamp 300, the sample preparation agent can be pressed further into the sample container 100, whereby then the cutting and stamping device 220 penetrates the lid or wall region 310. As soon as this has occurred, the biological sample material 230 can be pressed, by means of a further and more narrow stamp 510, through the sample preparation agent 200 out of the cutting and stamping device 220 and through the sample compartment 160 out of the sample container 100.

FIG. 5 concerns a further embodiment example of a sample container 500 according to the invention.

This embodiment example is essentially the same as the embodiment example shown in FIG. 1. As an example the sample container 500 also features a lid 540, a lateral wall region 520 and a base wall region 530. In the sample container 500 a sample compartment 560 is again provided that is encompassed by a drying compartment 580 that contains the hygroscopic substance 590.

In contrast to the embodiment examples shown so far a transversally running wall region 600 is furthermore provided in the sample compartment 560. The wall region 600 is arranged in the shown case approximately at middle height in the sample compartment 560. It however can also, without further ado, be located in another height position, for example directly in the area of an opening 40 of the sample compartment 560.

In the area 660, which is now closed by means of the transversally running wall 600 as well as the lateral wall 570 of the sample compartment 560 and the base 530 of the sample container 500, suitable reagents, particularly in liquid form 610, can be placed for processing, conservation or other treatments of the sample material that is not shown in this figure.

It is conceivable to provide a lysis buffer here with which the sample material is brought in contact with for the purpose of preparation of the processing in the laboratory. It is also conceivable to place reagents for additional processing steps. In this way time or procedural steps can be saved since the sample container 500 displayed in FIG. 5 offers the possibility of drying the sample material after preparation as well as also of executing initial processing steps in it after the penetration of the wall 600.

This embodiment furthermore permits in an advantageous way working contamination-free in a laboratory since the sample material does not have to be transferred into a further laboratory vessel. The contact between sample material and reagent can be established without that one has to reach into the closed system that is formed by sample container and sample preparation agent or that this closed system has to be opened.

It could also be conceivable that one would not only perform the primary processing of the sample material in this sample container, but that through the implementation of further compartments in this closed system for example a PCR reaction or an Elisa test could also be performed.

FIG. 6 presents a sample container 700 in which a drying compartment 780 that is implemented as a form part 785 is provided. The form part 785 is implemented as a thick-walled foil in which the hydroscopic substance 790 is embedded and which lines the sample container 700 in the lateral wall region 720 on the inside.

In the presented embodiment example the drying compartment 780 encompasses the sample compartment 760 without a wall being provided between the two compartments. This is not necessary in the presented embodiment example since there is no danger of contamination from the hydrsocopic substance 790 because it is embedded in the form part 785.

In the presented embodiment example the form part 785 that implements the drying element 780 is a type of foil or a sleeve that is insertable into the sample container 700. Conceivable are of course also other shapes.

Furthermore it is also conceivable, as was addressed above already, that the drying compartment is, in this embodiment example, manufactured externally and then inserted into the sample It is also just as well possible that the sample container and drying compartment are manufactured together, for example through sequential steps of an injection molding process.

The invention claimed is:

1. A device for the preparation and storage of biological sample material, the device comprising:

a sample container comprising an upper opening that can be closed by a lid, a lateral wall region, a base and a hygroscopic substance contained in the interior of the sample container for drying sample material in the sample container, wherein the sample container is partitioned into at least two compartments of which one is a sample compartment and the other is a drying compartment containing the hygroscopic substance, wherein the hygroscopic substance communicates with the interior of the sample compartment via a steam exchange connection, and wherein the sample compartment extends in a flush manner from the base of the sample container to an open upper end; and a sample preparation agent having a lower end that can be inserted into the sample container such that the lower end is disposed in the sample container in a defined position above and with a spacing to the open upper end of the sample compartment;

wherein at the lower end of the sample preparation agent there is provided a cutting or stamping device by means of which biological sample material can be obtained by guiding of the lower end through tissue, and wherein the cutting or stamping device on the lower end of the sample preparation agent and the open upper end of the sample compartment in the sample container are adapted to one another in such a manner that biological sample material obtained with the cutting or stamping device is located above the sample compartment subsequent to insertion of the sample preparation agent into the sample container and such that biological sample material is adapted to be inserted into the sample compartment or to fall into the sample compartment.

2. The device according to claim 1, wherein the sample compartment is encompassed by the drying compartment.

3. The device according to claim 1, wherein the drying compartment is implemented as a form part that contains the hygroscopic substance.

4. The device according to claim 3, wherein the form part consists of plastic in which the hygroscopic substance is embedded.

5. The device according to claim 3, wherein the drying compartment is put into the desired shape by means of pressing, sintering, or extruding the hygroscopic substance.

6. The device according to claim 1, wherein the sample compartment is delimited by at least one wall that is implemented in the sample container.

7. A device according to claim 1, wherein the sample compartment is separated by means of a transverse wall so as to form a separate area in which one or more reagents can be placed for the processing of the sample material.

8. The device according to claim 1, wherein the sample compartment is a hollow cylinder, implemented with spacing relative to a side wall region of the sample container, whose lower end borders the base of the sample container.

9. The device according to claim 1, wherein the sample container is closed by means of a penetrable lid.

10. The device according to claim 1, wherein the hygroscopic substance is selected from the group consisting of zeolite, silica gel and molecular sieve.

11. The device according to claim 1, wherein the sample container features a penetrable lid.

12. The device according to claim 1, wherein the lower end of the sample preparation agent closes the sample container after the insertion.

13. The device according to claim 1, wherein the device is a component of an ear mark for the marking of animals.

14. The device according to claim 1, wherein the sample compartment is closed in the area of its upper end by means of a penetrable wall section and wherein an opening is provided in the base below the sample compartment, the base covering the cross section of the drying compartment.

* * * * *